United States Patent [19]

Sato et al.

[11] Patent Number: 5,414,174
[45] Date of Patent: May 9, 1995

[54] SIDE-CHAIN ALKYLATION METHOD

[75] Inventors: Toshio Sato; Ikuo Ito; Hiromichi Yamaguchi; Kyoichi Takeda, all of Kashima, Japan

[73] Assignee: Sumikin Chemical Co., Ltd., Japan

[21] Appl. No.: 73,162

[22] Filed: Jun. 7, 1993

[30] Foreign Application Priority Data

Jun. 5, 1992 [JP] Japan ................. 4-171772

[51] Int. Cl.$^6$ .............................................. C07C 2/66
[52] U.S. Cl. ..................... 585/467; 585/446; 585/452
[58] Field of Search ............ 585/452, 453, 446, 457, 585/461

[56] References Cited

U.S. PATENT DOCUMENTS

| | | | |
|---|---|---|---|
| 2,993,050 | 7/1961 | Gleason et al. | 585/452 |
| 3,244,758 | 4/1966 | Eberhardt | 585/452 |
| 3,468,970 | 9/1969 | Screttas | 585/452 |
| 3,651,161 | 3/1972 | Waragai et al. | 585/452 |
| 3,742,077 | 6/1973 | Kamienski et al. | 585/452 |
| 5,030,784 | 7/1991 | Slaugh | 585/452 |

*Primary Examiner*—Anthony McFarlane
*Attorney, Agent, or Firm*—Harris Beach & Wilcox

[57] ABSTRACT

There is disclosed a side-chain alkylation reaction wherein an alkyl aromatic compound having a benzyl hydrogen is reacted with unsaturated hydrocarbons to produce a desired target product with excellent selectivity. The reaction is conducted in the presence of an alkyl ether and an alkaline metal catalyst. In comparison with conventional methods, it was observed that target selectivity was improved remarkably when equimolar addition of the reactants was employed, that very little catalyst was needed, and that the catalyst could be treated as a linear or uniform system, allowing the reaction to be easily scaled to meet industrial requirements.

16 Claims, No Drawings

SIDE-CHAIN ALKYLATION METHOD

BACKGROUND OF THE INVENTION

This invention relates to a side-chain alkylation method for alkyl aromatic hydrocarbons containing benzyl hydrogen.

Field of the Invention

The side-chain alkylated compounds in a group of alkyl aromatic hydrocarbons possess versatile applications as raw materials, as surface active agents, or as intermediate compounds such as alkylnaphthalene, alkylphenanthrene, alkylanthracene, or the like. In particular, 1,5-dimethylnaphthalene, an alkylated, cyclized, and dehydrogenated reaction product of o-xylene and 1,3-butadiene, is industrially useful as a source of 2,6-dimethylnaphthalene, a raw material for the production of 2,6-naphthalen-dicarboxylic acid.

A method utilizing alkaline metals as catalyst is well-known in which an alkyl aromatic hydrocarbon containing benzyl hydrogen is side-chain alkylated with unsaturated hydrocarbons.

For example, the following methods have been disclosed: (1) reaction of an alkyl aromatic hydrocarbon and ethylene in the presence of a catalyst comprising potassium and biphenyl or alkyl biphenyl (Japanese patent Publication No.51-17539); (2) reaction of an alkyl aromatic hydrocarbon and ethylene in the presence of a catalyst comprising sodium metal and pyrene (Japanese Patent Publication No.51-17540); and (3) reaction of an alkyl substituted benzene and 1,3-butadiene in the presence of a catalyst containing definite ratio of potassium and sodium and also by using naphthalene or an alkyl substituted naphthalene as a promoter (Japanese Patent Publication No.51-8930).

Moreover a detailed study was reported on an addition reaction of isoprene, propylene or ethylene with alkylbenzene or alkylnaphthalene using alkaline metal catalysts (J. Org. Chem. Vol. 30, p. 280, 1965; J. Am. Chem. Soc. Vol. 82, p. 4912, 1960, or J. Org. Chem. Vol. 34, p.2106, 1969).

Also, the addition of 1,3-butadiene to alkyl aromatic hydrocarbons, particularly for producing 1:1 adduct in the presence of alkaline metal catalysts has been reported (J. Org. Chem. Vol.30, p.82, 1965).

When the 1:1 adduct is performed with an unsaturated hydrocarbon and then synthesized to a side-chain alkylation reaction with aromatic hydrocarbons containing a benzyl hydrogen, (the adducts involve the α-position carbon), a relatively large amount of alkaline metal is required to achieve a given yield of target products. Furthermore, the recovery ratio of the aromatics used is relatively low and the conversion ratio is required to be controlled at as low a level as possible. Moreover, certain operations need to be performed while distributing the alkaline metal catalysts, causing additional technical problems.

It is especially difficult to selectively obtain a desired reaction product when adducts comprising a 1:1 composition of aromatic hydrocarbons having a plurality of alkyl radicals and unsaturated hydrocarbons are synthesized.

SUMMARY OF THE INVENTION

Accordingly, it is an object of the present invention to provide a method for selectively producing a target substance in a side-chain alkylation reaction produced by the equimolar composition of aromatic hydrocarbons containing benzyl hydrogen and unsaturated hydrocarbons.

As a result of continuous and diligent research and experiments, the present inventors have discovered a new method wherein an alkyl ether in which an alkaline metal catalyst is soluble is employed to substantially improve target selectivity with a 1:1 composition of adducts comprising aromatic hydrocarbons having a benzyl hydrogen and unsaturated hydrocarbons, the target being produced by a side-chain alkylation reaction.

Namely, according to the present invention, alkyl aromatic compounds are alkylated by unsaturated hydrocarbons in the presence of alkyl ether and alkaline metal catalysts.

It is necessary that the alkyl ether employed in the present invention be capable of dissolving the alkaline metal catalysts. Any of the following can be used: diethylether, di-isopropylether, ethyleneglycoldimethylether, diethyleneglycol-dimethylether, tetrahydrofuran, methyltetrahydrofuran, dioxan, or diphenylether. They can also be used individually or in combination. Among these, tetrahydrofuran is remarkably effective, and is associated with higher target selectivity produced with 1:1 adducts, even with a relatively high conversion, than is seen with the conventional method.

It is not required that the alkyl ether fully dissolve the alkaline metal catalysts. The optimum amount of alkyl ether ranges from 0.01 to 100 times that of the alkyl aromatics, preferably it ranges from 0.1 to 10 times the mass of the alkyl aromatics. It is proved that the target selectivity produced with the 1:1 adduct may be reduced if too little alkyl ether is used. On the other hand, if excessive alkyl ether is used, the mass efficiency will be reduced, impairing industrial applicability.

The alkaline metal catalyst can be any type of catalyst as long as it functions as an anion catalyst. Any of the following can be used; sodium, potassium, lithium, cesium, or their hydrides, their adducts with alkyl and aromatic compounds or complex compounds therewith or alkyl ether. They can be used individually or in combination.

The alkaline metal required ranges from 0.05 to 50 mol % catalyst in the alkyl aromatic hydrocarbons; preferably it ranges from 0.5 to 15 mol %. If too little alkaline metal catalyst is used, the addition reaction rate of unsaturated compounds becomes slow, resulting in side reactions easily. On the other hand, if excessive catalyst is present, the target selectivity produced by the equimolar addition reaction may be improved, but the practice is uneconomical.

Aromatic compounds are effective promoters of the above-noted side-chain alkylation reaction. While it is known that a combination of an alkaline metal catalyst and aromatic compounds is effective, the inventors have discovered that side-chain alkylation reaction is even more effective preceded by the addition of an alkyl ether, even if the ether has a different chemical composition or is derived from a different reaction system.

The aromatic compounds used as a promoter in the reaction can be naphthalene, biphenyl, terphenyl, pyrene, phenanthrene, or their alkyl derivatives. The amount of required aromatic compounds as a promoter can be from 0.01 mol to an equimolar amount per mol of alkaline metal catalyst, it normally ranges from 0.05 mol to 0.5 mol. If too little promoter were used, effectiveness would be reduced. On the other hand, excessive promoter will not affect the chemical reaction but is undesirable for economic and operational reasons.

The unsaturated hydrocarbons, if they are chain-form or ring-form unsaturated hydrocarbons, can be of any type. For example, the unsaturated hydrocarbons, ranging from low molecular weight such as ethylene, styrene, propylene, or butylene to about $C_{20}$ compounds can be used. Moreover, they can include diene groups including 1,3-butadiene, 2-methyl-1,3-butadiene, pentadiene groups and hexadiene groups and also ring forms such as cyclohexane, cyclohexadiene or acenaphthylene, or the like. In a case when these compounds are added to a reaction system to initiate the reaction, it is necessary to determine the addition speed of reactant by correlation with the reaction rate. In general, a slow adding speed tends to give good result. Since the aforementioned unsaturated hydrocarbons are highly soluble in alkyl ethers, the reaction can effectively proceed in the presence of an alkyl ether.

Any alkyl aromatic compounds having a benzyl hydrogen can be used, preferably toluene, xylene, trimethylbenzene, ethylbenzene, or ethyltoluene groups, ethylxylene groups, diethylbenzene groups or alkyl benzene groups; alkylnaphthalene such as methylnaphthalene, ethylnapthalene, or dimethylnaphthalene and derivatives thereof; or other types of compounds including alkylbiphenyl derivatives, alkylanthracene derivatives, or alkylbiphenylether.

According to the present invention, the alkyl aromatic compounds are alkylated by unsaturated hydrocarbons in the presence of alkyl ether and alkaline metal catalysts, the addition of which precedes the principal reaction, that is excellent target selectivity is produced by a 1:1 additional reaction of the unsaturated compounds with a compound having a benzyl hydrogen. The method of the invention is especially advantageous in reaction systems in which side reactions can easily take place. This advantage can be more clearly realized in a mixture of aromatic compounds having a plurality of alkyl radicals such as xylene, trimethylbenzene, ethyltoluene derivatives, ethyl-p-xylene, or the like. The same advantage can be recognized with unsaturated hydrocarbons. For example, the present method is highly suitable for the 1,3-butadiene addition reaction.

Although the unsaturated compounds are generally added to a mixed system of alkyl aromatic compounds, alkyl ether and the alkaline metal catalysts, the order of mixing these compound may be not ignored.

It is disadvantageous if the amount of unsaturated hydrocarbon is too little, because yield decreases, even though target selectivity produced with 1:1 adduct increases. On the other hand, if too much unsaturated hydrocarbon is added, di-adduct will easily be formed and excessive consumption of the starting material will result. Hence, depending upon the nature of the reaction system, the unsaturated hydrocarbons will be less than mol equivalent to the alkyl aromatic compounds, preferably it will be optimum from 0.3 to 0.7 mol.

It is not necessary to maintain the reaction temperature above the melting point of the alkaline metal, as is done conventionally. The reaction can be even conducted at lower temperatures, normally at a temperature ranging from 30° to 100° C.

The alklylation reaction can be performed under either excess pressure, reduced pressure, or atmospheric pressure, or by a batch process or a continuous process.

It is important to provide raw material reactant promoter and the alkyl ether removing as much water as possible for the reaction.

After the side-chain alkylation reaction is completed, the target products can be separated by known techniques such as distillation, crystallization, or the like with or without deactivation of the catalysts.

DETAILED DESCRIPTION OF A PREFERRED EMBODIMENT

Embodiments 1 through 3

Into a 300 ml flask with a stirrer, ethyl-p-xylene 1 mol, sodium 0.020 mol and potassium 0.013 mol as an alkaline metal catalyst, and biphenyl 0.0083 mol as a promoter were placed, and heated at 110° C. while stirring for 5 minutes. After cooling down to 60° C., tetrahydrofuran was added while stirring. At the same temperature, namely 60° C., 1,3-butadiene was fed for 6 hours at a flow rate of 0.1 mol/hour. Water was then added to deactivate the catalysts, and the sample was analyzed by gas chromatography. The results obtained are listed in Table 1. The conversion (%) indicates the analyzed value (in terms of area percentage) of the raw material (ethyl-p-xylene) after the reaction, and the selectivity (%) indicates a ratio (in terms of area percentage) of the target product (5-p-xylyl-hexene) in the butadiene adducts.

TABLE 1

| | | 5-(p-xylyl)-hexene | |
|---|---|---|---|
| Embodiment | solvent (ml) | conversion (%) | selectivity (%) |
| 1 | tetrahydrofuran: 50 | 49.2 | 66.5 |
| 2 | tetrahydrofuran: 100 | 48.2 | 72.2 |
| 3 | tetrahydrofuran: 200 | 46.2 | 73.3 |

Comparison 1

Similar experiments were performed as in embodiment 2, except that the reaction temperature was 120° C., and solvent was not utilized.

After the catalyst was deactivated, the sample was analyzed by gas chromatography. Results are listed in Table 2. The conversion (%) indicates the analyzed value (in terms of area percentage) of the raw material (ethyl-p-xylene) after the reaction, and the selectivity (%) indicates a ratio (in terms of area percentage) of the target product (5-p-xylyl hexene) in the butadiene adducts.

TABLE 2

| Comparison 1 5-(p-xylyl)-hexene | |
|---|---|
| conversion (%) | selectivity (%) |
| 44.5 | 34.2 |

Embodiments 4 through 6

Ethyl-p-xylene 1 mol, alkaline metal, and biphenyl 0.0083 mol as a promoter were fed in to a 300 mol flask with a stirrer, and heated at 110° C. for 5 minutes while stirring after cooling down to 60° C., tetrahydrofuran, as the alkyl ether, 100 ml was added and stirred. At 60° C.,1-3-butadiene was added at a flow rate Of 0.1 mol/hour for 6 hours.

After the catalyst was deactivated, the sample was analyzed by gas chromatography. Obtained results are shown in Table 3. The conversion (%) indicates the analyzed value (in terms of area percentage) of the starting material (ethyl-p-xylene) after the reaction, and the selectivity (%) indicates a ratio (in terms of area percentage) of the target product (t-p-xylyl-hexene) in the butadiene adducts.

TABLE 3

| embodiment | alkaline metal (mol) Na | alkaline metal (mol) K | t-(p-xylyl-hexene) conversion (%) | t-(p-xylyl-hexene) selectivity (%) |
|---|---|---|---|---|
| 4 | 0 | 0.018 | 51.2 | 69.0 |
| 5 | 0.011 | 0.007 | 46.5 | 70.8 |
| 6 | 0.018 | 0 | 45.2 | 51.3 |

Embodiment 7

Similar experiments were carried out as in embodiment 2, except that ethylbenzene was used instead of the alkyl substituted benzene.

After the catalyst was deactivated, the sample was analyzed by gas chromatography. Table 4 shows the result. The conversion (%) indicates the analyzed value (in terms of area percentage) of the raw material (ethyl benzene) after the reaction, and the selectivity (%) indicates a ratio (in terms of area percentage) of the target product (5-phenylhexene) in the butadiene adducts.

TABLE 4

| | 5-phenyl-hexene | |
|---|---|---|
| | conversion (%) | selectivity (%) |
| Embodiment 7 | 43.1 | 75.2 |

Embodiments 8 and 9

Similar experiments were performed as in embodiment 2 except that biphenyl was not used as a promoter.

After the catalyst was deactivated, a sample was analyzed by gas chromatography. Results are listed in Table 5. The conversion (%) indicates the analyzed value (in terms of area percentage) of the raw material (ethyl-p-xylene) after the reaction, and the selectivity (%) indicates a ratio (in terms of area percentage) of the target product (5-p-xylyl-hexene) in the butadiene adducts.

TABLE 5

| Embodiment | promoter (each 0.8 g) | 5-(p-xylyl)-hexene conversion (%) | 5-(p-xylyl)-hexene selectivity (%) |
|---|---|---|---|
| 8 | naphthalene | 47.4 | 71.9 |
| 9 | phenanthrene | 48.3 | 64.8 |

TABLE 6

| Comparison 2 5-(p-xylyl)-hexene | |
|---|---|
| conversion (%) | selectivity (%) |
| 31.0 | 29.4 |

As described above, according to the present invention, target selectivity associated with the addition reaction is remarkably improved in comparison with conventional methods. Furthermore, only a very small amount of alkaline metal catalyst is required, and the catalyst can be treated, as a homogeneous system, so that the operation of the process can be easily conducted and the practice can be applied to large industrial production.

While this invention has been explained with reference to the process described herein, it is not confined to the details as set forth and this application is intended to cover any modifications and changes as may come within the scope of the following claims.

What is claimed is:

1. A side-chain alkylation method to alkylate an alkyl aromatic compound, comprising the step of reacting the alkyl aromatic compound with an unsaturated hydrocarbon in the presence of an ether selected from the group of an alkyl ether and an alkyl aromatic ether, and in the presence of an alkaline metal catalyst and a promoter selected from the group of naphthalene, biphenyl, terphenyl, anthracene, pyrene, phenanthrene.

2. The method according to claim 1 wherein the ether is tetrahydrofuran.

3. The method according to claim 1, wherein the unsaturated hydrocarbon is 1,3-butadiene.

4. The method according to claim 1, wherein the alkaline metal catalyst is selected from the group of sodium, potassium and an alkyl derivative thereof.

5. The method according to claim 1, wherein the alkyl aromatic compound is an alkyl substituted aromatic hydrocarbon.

6. The method according to claim 1, wherein the alkyl aromatic compound has a benzyl hydrogen.

7. A method of alkylating an alkyl aromatic compound, comprising the steps of:
dissolving an alkaline metal catalyst in an alkyl ether;
adding to said alkyl ether and said catalyst an unsaturated hydrocarbon and an alkyl aromatic compound having a benzyl hydrogen;
reacting said added hydrocarbon and said alkyl aromatic compound to yield a side chain alkylation target product in the presence of a promoter selected from the group of naphthalene, biphenyl, terphenyl, anthracene, pyrene, phenanthrene; and
recovering said target product from said alkyl ether and said catalyst.

8. The method according to claim 7, wherein said alkyl ether and said alkyl aromatic compound are in a mass ratio of 0.1 to 10.

9. The method according to claim 7, wherein said alkaline metal catalyst comprises 0.5–15 mol % of said alkyl aromatic compound.

10. The method according to claim 7 wherein said alkyl ether is tetrahydrofuran.

11. The method according to claim 7, wherein said unsaturated hydrocarbon is 1,3-butadiene.

12. The method according to claim 7, wherein the alkaline metal catalyst is selected from the group of sodium, potassium and an alkyl derivative thereof.

13. The method of alkylating an alkyl aromatic compound, comprising the steps of:
dissolving an amount of an alkaline metal catalyst selected from the group of sodium, potassium and an alkyl derivative thereof in tetrahydrofuran;
adding 1,3-butadiene and ethyl-p-xylene to said tetrahydrofuran and said catalyst;
reacting said added 1,3-butadiene and said ethyl-p-xylene in a presence of a promoter selected from the group of biphenyl, terphenyl, anthracene, pyrene, phenanthrene, and an alkyl derivative thereof to yield 5-(p-xylyl)-hexene.

14. The method according to claim 13, wherein said promoter is biphenyl.

15. The method in accordance with claim 1, wherein said step of reacting yields a target product having a saturated alkyl side chain, said target product and said alkyl aromatic compound having an equal number of aromatic rings.

16. The method in accordance with claim 7, wherein said target product has a saturated alkyl side chain, said target product and said alkyl aromatic compound having an equal number of aromatic rings.

* * * * *